United States Patent [19]

Hirschmann et al.

[11] Patent Number: 5,004,849

[45] Date of Patent: Apr. 2, 1991

[54] MANUFACTURE OF PERCHLOROETHYLENE AND TRICHLOROETHYLENE BY CATALYTIC OXYCHLORINATION, AND IMPROVED CATALYSTS THEREFOR

[75] Inventors: Robert P. Hirschmann; William Q. Beard, Jr., both of Wichita; Eric L. Mainz, Colwich; Earl B. Smith, Newton, all of Kans.; Barry M. Little, Castlewood, S. Dak.

[73] Assignee: Vulcan Chemicals, Wichita, Kans.

[21] Appl. No.: 451,303

[22] Filed: Dec. 15, 1989

[51] Int. Cl.$^5$ .................... C07C 17/15; C07C 19/156
[52] U.S. Cl. .................................... 570/224; 502/225
[58] Field of Search ........................................ 570/224

[56] References Cited

U.S. PATENT DOCUMENTS

| | | |
|---|---|---|
| 2,636,864 | 4/1953 | Pye et al. |
| 3,267,162 | 8/1966 | Bohl . |
| 3,296,319 | 1/1967 | Bohl et al. |
| 3,360,483 | 12/1967 | Diamond et al. |
| 3,427,359 | 2/1969 | Reetenwald et al. |
| 3,624,170 | 11/1971 | Wakiyama et al. |
| 3,657,367 | 4/1972 | Blake et al. |
| 4,124,534 | 11/1978 | Leitert et al. |
| 4,414,136 | 11/1983 | Convers . |
| 4,463,200 | 7/1984 | Beard, Jr. et al. |
| 4,587,230 | 5/1986 | Cavaterra et al. |

FOREIGN PATENT DOCUMENTS 1386023  5/1965  France .
1256074  12/1971  United Kingdom .

OTHER PUBLICATIONS (Abstract), German Publ. 1,917,041–CA 72:31208 b.
(Abstract), German Publ. 1,917,042–CA 72:31207p.
(Abstract), German Publ. 2,226,657, CA 78:71395d.
(Abstract), German Publ. 1,920,685, CA 72:71145y.
(Abstract), Braz. Pedido PI BR 82 00,180, CA 98:106780t.
(Abstract), Spanish Patent No. 396,467–CA 83:78549u.
(Abstract), Spanish Publ. 396,465–CA 83:78548t (1975).

*Primary Examiner*—Howard T. Mars
*Attorney, Agent, or Firm*—Burns, Doane, Swecker & Mathis

[57] ABSTRACT

A superior catalyst for the oxychlorination of $C_2$ hydrocarbon feeds comprises a mixture of copper chloride and alkali metal chloride, for instance, potassium chloride, and preferably also magnesium chloride, which mixture is deposited on an alumina support having a surface area in excess of 20 and less than 100 $m^2/g$. The thermal stability of such a catalyst composition can be further improved by incorporating 0.2 to 5 percent silica in the alumina support. The use of such microspheroidal catalyst in the production of perchloroethylene and trichloroethylene by oxychlorination of a $C_2$ hydrocarbon feed in a fluidized bed reactor results in particularly good process efficiencies in terms of high HCl conversion, and good flexible selectivity to specifically desired product, reduced burning, long on-stream times, and relatively low corrosion rates.

5 Claims, 3 Drawing Sheets

MANUFACTURE OF PERCHLOROETHYLENE AND TRICHLOROETHYLENE BY CATALYTIC OXYCHLORINATION, AND IMPROVED CATALYSTS THEREFOR

BACKGROUND OF THE INVENTION

1. Field of the Invention

The invention relates to the production of perchloroethylene and trichloroethylene by catalytic oxychlorination of $C_2$ hydrocarbons or their partially chlorinated derivatives, to catalysts useful in such oxychlorination processes, and to processes for making such catalysts.

2. General Background and Summary of the Prior Art

Perchloroethylene, $C_2Cl_4$, and trichloroethylene, $C_2HCl_3$, are chlorinated hydrocarbons which have been widely used as solvents in dry cleaning textiles, in degreasing metal parts, in various solvent extraction processes, in compounding rubber cements, and in various other operations. Perchloroethylene is relatively stable, so its use is currently much less severely restricted by anti-pollution regulations than is the use of most other chlorinated solvents. Trichloroethylene is a potentially valuable intermediate for manufacturing chlorofluorocarbon replacements which are less damaging to the atmospheric ozone layer.

It has been common to produce perchloroethylene simultaneously with trichloroethylene by catalytic oxychlorination of ethane, ethylene or a partially chlorinated derivative thereof, i.e., by reacting such a feedstock with chlorine or hydrogen chloride and air or oxygen at a suitable elevated temperature in the presence of a suitable solid catalyst, the catalyst being maintained in the reaction zone either as a fixed bed or, more preferably, as a fluidized bed.

Typically, such oxychlorination catalysts are compositions that comprise a catalytic amount of a metal having a variable valence, notably copper, as well as an alkali metal, notably potassium, supported on a suitable carrier. Carriers used commercially in the past have included highly calcined Fuller's earth (an adsorbent clay) such as "Florex" or, preferably, synthetic activated aluminas. See, for instance, U.S. Pat. No(s). 3,267,162, 3,296,319 and 4,463,200. Fuller's earth is essentially a porous magnesium-aluminum silicate containing small proportions of oxides of iron, calcium, potassium and titanium. By contrast, synthetic activated alumina consists essentially of alumina with virtually no significant impurities or at the most only a very small proportion of silica.

Researchers working on catalytic oxychlorination processes in the prior art have in some instances expressed a preference for the use of low-surface-area alumina as catalyst supports, i.e., for supports having a surface area below 10 $m^2/g$ or more especially between 2 and 5 $m^2/g$ (as in U.S. Pat. No. 4,124,534), while in other instances they have expressed a preference for high-surface-area alumina as catalyst supports, i.e., for supports having a surface area of at least 100 $m^2/g$ (as in U.S. Pat. No. 4,463,200). Low-surface-area supports have been recommended mainly because they were thought to result in higher HCl conversions and lower carbon burning (see, for instance, U.S. Pat. No. 3,427,359 and French Patent No. 1,386,023), whereas high-surface-area supports have been recommended because they were thought to contribute to an increased selectivity of the reaction toward the production of perchloroethylene as the desired product and a reduced formation of undesirable 1,1,2-trichloroethane and unsymmetrical tetrachloroethane, as indicated in U.S. Pat. No. 4,463,200.

However, catalysts comprising a low-surface-area support have been found to be relatively unstable in that such supports possess only a relatively small number of binding sites for retaining the active metal salts in the composition, and the resulting loss of the metal salts from such catalysts has been found to constitute a significant factor in causing corrosion of the metal reactors in which such oxychlorination reactions are generally carried out. In addition, especially when low-surface-area supports such as diatomaceous earth or other silica-aluminas are used, high selectivities to perchloroethylene and trichloroethylene are not obtained at reasonable temperatures.

On the other hand, catalysts comprising a high-surface-area support, especially when used at temperatures near or above 400° C. which are required to obtain good selectivity for the production of perchloroethylene and trichloroethylene, cause substantial oxidation of the feed material with a concomitant formation of unwanted carbon oxides, especially when ethane or ethylene are used as the feed, and in particular under conditions favoring the production of trichloroethylene.

SUMMARY OF THE INVENTION

Accordingly, a primary object of the present invention is to provide an improved oxychlorination process for the production of perchloroethylene and trichloroethylene, which process avoids or substantially alleviates the disadvantages of the prior art discussed above.

Another object is to provide improved catalyst compositions for use in the production of perchloroethylene and trichloroethylene by oxychlorination, such that the disadvantages and problems heretofore encountered in the prior art may be avoided or substantially alleviated.

A more particular object is to provide an oxychlorination process for the production of perchloroethylene and trichloroethylene from ethane, ethylene or partially chlorinated derivatives thereof, wherein corrosion of metal reactor surfaces is avoided or minimized.

A corollary object is to provide improved catalyst compositions for the production of perchloroethylene and trichloroethylene by oxychlorination, which results in improved overall feed conversions and reduced reactor corrosion, as well as flexibility allowing efficient use of the same catalyst under conditions selected to maximize the production of either perchloroethylene or trichloroethylene.

Another particular object is to provide a process for making an improved catalyst composition for use in the production of perchloroethylene and trichloroethylene by oxychlorination, which composition possesses improved long-term surface area stability at elevated oxychlorination temperatures and consequently remains operable over extended periods of time, without becoming sticky due to salt overload such as has been known to occur when the surface area of a catalyst support becomes diminished in the process.

Another object is to provide an improved catalyst composition for the production of perchloroethylene and trichloroethylene by oxychlorination of ethane, ethylene or a partially chlorinated derivative thereof, which catalyst gives improved performance in terms of reduced combustion of the organic feed stock, and usually also in terms of increased conversion of hydrogen chloride or chlorine as well as higher total selectivity to the desired end products.

In accordance with one aspect of the present invention, an improvement is provided in the production of perchloroethylene and trichloroethylene by catalytic oxychlorination of at least one $C_2$ hydrocarbon or a partially chlorinated derivative thereof, which improvement is based on the use of a microspheroidal catalyst composition which comprises a catalytic amount of a mixture of copper chloride and alkali metal chloride deposited on an especially selected support, the support being an alumina having a surface area closely controlled within a range which is in excess of 20 and less than 100 m$^2$/g, preferably between about 20 and 80 m$^2$/g, and most preferably between about 25 and 60 m$^2$/g. When such a catalyst composition is to be used in a fluidized bed process, it is desirably composed of particles having an average particle diameter of between about 30 and about 70 microns. The copper chloride-alkali metal chloride catalyst mixture is loaded onto this alumina support at a concentration of between about 10 and about 25 weight percent and the ratio of copper chloride to alkali metal chloride in the catalyst mixture is in the range from 0.5:1 to 5.0:1, preferably from 0.5:1 to 3.0:1, and most preferably from 1.2:1 to 3.0:1, calculating the copper chloride as $CuCl_2$.

In accordance with another aspect of the present invention, an improved catalyst composition for such an oxychlorination process is provided by using as the catalyst carrier or support a substantially pure high-surface-area gamma-alumina having from 0.2 to 10 weight percent silica incorporated therein. While thermal stabilization of alumina by incorporation of silica is not broadly new and has in fact been practiced in the manufacture of supports for platinum catalysts used in automotive exhaust canisters, no such stabilization of alumina supports is known to have been practiced in the production of oxychlorination catalysts and was in fact thought to have been unnecessary because oxychlorination reactions are normally run at temperatures well below the normal transition temperature of 1200° C. at which gamma-alumina changes over to the low-surface-area alpha form (see, for example, Allen Russell, "Alumina Properties", Technical Paper No. 10, Alcoa Research Laboratories, 1953, page 6).

Figure 1:
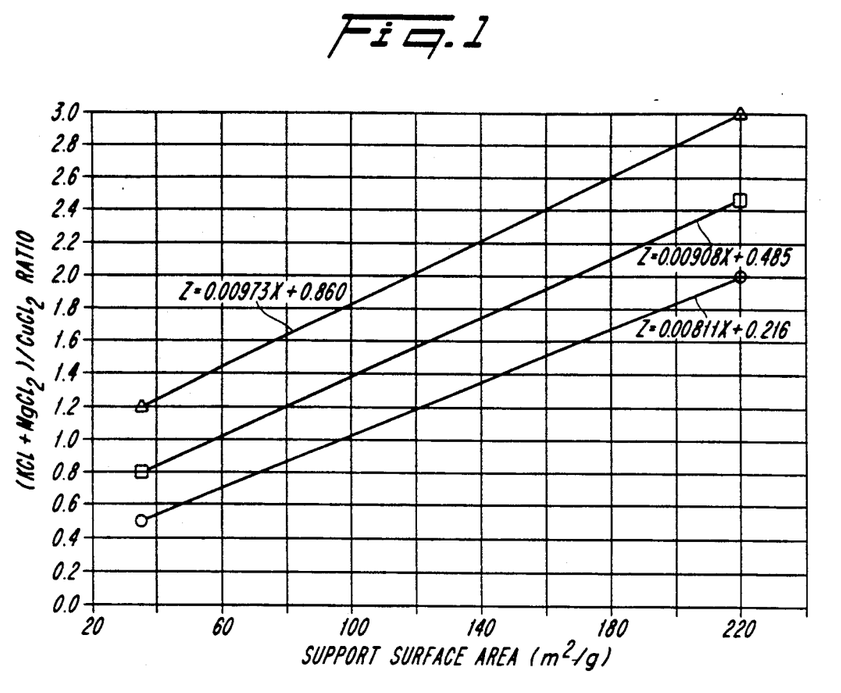
FIG. 1 is a graph showing the correlation between a suitable ratio of potassium chloride plus magnesium chloride/copper chloride and surface area of the alumina support used in the catalyst composition.

Yet another aspect of the invention involves an improved oxychlorination catalyst composition that comprises a copper chloride-alkali metal chloride catalyst mixture loaded on a support consisting essentially of an activated alumina or an activated alumina stabilized against thermal degradation by the inclusion of a small amount of silica, wherein a significant further improvement is obtained by the addition of a magnesium salt such as magnesium chloride to the catalyst mixture. When magnesium is included in the catalyst mixture, it is present in an amount resulting in a weight ratio of alkali metal chloride (e.g., potassium chloride) to magnesium chloride from 0.5:1 to 2.0:1, preferably 0.8:1 to 1.2:1, and most preferably between 0.95:1 and 1.05:1, irrespective of the surface area of the catalyst support. On the other hand, the desirable ratio of (potassium chloride + magnesium chloride)/copper chloride is dependent on the surface area and has been found to be ideally described, with very high correlation, by equation (1):

$$Z(preferred) = 0.00908X + 0.485 \quad (1)$$

where Z is the ratio of (potassium chloride + magnesium chloride)/cupric chloride and X is the surface area of the alumina support in square meters per gram. An upper value where good results can still be obtained is described by the equation:

$$Z(upper) = 0.00973X + 0.860$$

and a lower value of the same useful nature is described by the equation:

$$Z(lower) = 0.00811X + 0.216.$$

A graph corresponding to these equations is shown in FIG. 1.

Figure 2:
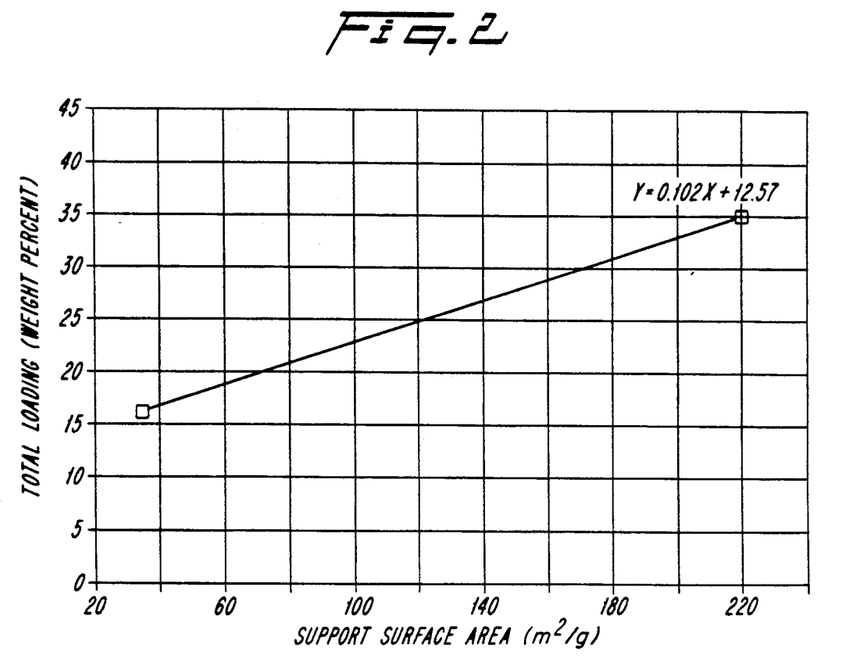
FIG. 2 is a graph showing the correlation between a suitable total catalyst loading and the surface area of the alumina support used in the catalyst composition.

The optimum loading also varies with surface area and has been found by linear regression to follow, again with very high correlation, the equation (2):

$$Y(preferred) = 0.102X + 12.57 \quad (2)$$

where Y is the total catalyst loading in weight percent and X is the surface area of the catalyst support in square meters per gram. A graph representing this equation is shown in FIG. 2. A variation from this equation of plus or minus about 20 percent gives satisfactory results. Higher loadings risk agglomerization of the catalyst while lower loadings show reduced activity.

The useful range of surface areas described by the above equations is from above about 20 to less than about 100 m$^2$/g of support, but for best results overall in accordance with the present invention the use of alumina supports having a surface area of from about 25 to about 60 m$^2$/g is preferred.

THE DRAWINGS

Referring to the drawings—

In reading this specification and claims, it should be understood that all proportions and percentages of materials are stated on a weight basis throughout unless some other basis is indicated explicitly or implicitly.

DESCRIPTION OF THE PREFERRED EMBODIMENTS

Perchloroethylene and trichloroethylene may be produced by catalytically oxychlorinating an organic feedstock comprising a $C_2$ hydrocarbon or an incompletely chlorinated derivative thereof or a mixture comprising two or more such hydrocarbons and/or incompletely chlorinated derivatives thereof. Preferred feed materials include ethane, ethylene, ethyl chloride (monochloroethane), ethylene dichloride (1,2-dichloroethane), and mixtures containing two or more of these compounds. Recycle chlorocarbon streams containing these compounds can, of course, be used as feed sources. As used herein, the term "$C_2$ hydrocarbon" means and includes ethane, ethylene and any incompletely chlorinated derivative of any such hydrocarbon containing fewer chlorine atoms than the desired product, as well as any mixture comprising two or more of these "$C_2$ hydrocarbons".

When perchloroethylene is produced by catalytic oxychlorination, i.e., by reaction of the organic feedstock with hydrogen chloride or chlorine and oxygen, a substantial amount of trichloroethylene is also produced in addition to by-products, e.g., some lower boiling compounds and some higher boiling compounds as well as some carbon monoxide and carbon dioxide. Because the production of perchloroethylene and trichloroethylene by oxychlorination is a highly exothermic process, it is best carried out using a solid catalyst in a fluidized bed which, unlike a fixed bed, minimizes the formation of undesirable hot spots and facilitates the removal of the heat of reaction by means of heat exchangers, as is otherwise well known in the art (see, for example, M. Leva, "Fluidization", McGraw-Hill, 1959, pp 6, 208–209).

Such oxychlorination is desirably carried out at a reaction temperature of between about 370° and about 470° C., preferably between about 400° and about 430° C. Atmospheric, subatmospheric or superatmospheric reaction pressures may be used, but preferably the reaction pressure is maintained between about 1 and about 20 atmospheres, and more preferably between about 1 and about 6 atmospheres.

The oxychlorination reaction is generally conducted for a time sufficient to maximize the production of perchloroethylene and trichloroethylene based on carbon utilization. The superficial reaction zone residence time may suitably be from several seconds to several minutes, e.g., from about 2 seconds up to about 1 minute, and preferably from about 10 up to about 30 seconds.

Oxygen may be supplied to the reaction as pure oxygen gas or more commonly as an oxygen-containing gas, e.g., air or oxygen-enriched air. As is otherwise well known in the art, the ratio of total feed of oxygen to total feed of organic feedstock is a variable number which depends upon the specific composition of the feed and other process design factors. The oxychlorination reaction may be conducted with an amount of molecular oxygen that is at least equal to the stoichiometric amount required to completely oxychlorinate the organic feed to the ratio of trichloroethylene to perchloroethylene desired while at the same time converting substantially all displaced hydrogen to water.

More typically, the amount of oxygen supplied ranges between this stoichiometric amount and up to about 200 percent in excess of this amount, preferably from about 10 to about 50 percent in excess of stoichiometric. For instance, when making perchloroethylene by oxychlorinating ethylene, the reaction may be described by the equation $$C_2H_4 + 4HCl + 2O_2 \rightarrow C_2Cl_4 + 4H_2O$$

In such a case, it is preferred to use from 2.2 to 3 moles of oxygen per mole of ethylene feed.

In addition to the organic feedstock and oxygen, hydrogen chloride or chlorine or both are also supplied to the reaction zone. The ratio of total feed of chlorine and/or hydrogen chloride to total organic feedstock again is a variable number which depends upon the specific composition of the feed and other process design factors, as is well known in the art. The oxychlorination reaction is typically conducted with an amount of chlorine and/or hydrogen chloride adjusted to reflect the desired ratio of trichloroethylene and perchloroethylene that is at least equal to about 50 percent of the stoichiometric amount required to oxychlorinate the organic feedstock completely to perchloroethylene. For example, when ethylene dichloride is catalytically oxychlorinated to perchloroethylene it is preferred to maintain the mol ratio of hydrogen chloride to ethylene dichloride above about 1.6, e.g., of from between about 1.6 to about 1.9, while maintaining the mol ratio of oxygen to ethylene dichloride between about 1.5 and about 2.2.

The essence of the present invention lies in providing a special, improved catalyst composition comprising a catalytic amount of a copper chloride-alkali metal chloride mixture deposited on microspheroidal particles of activated alumina having a carefully selected surface area, and in conducting the oxychlorination reaction in contact with a fluidized bed comprising such microspheroidal catalyst particles. In preferred catalyst compositions, the alumina support is stabilized against thermal or thermochemical degradation by the deliberate inclusion of a small amount of silica in the alumina, and a particularly preferred composition comprises the inclusion of a certain proportion of magnesium chloride as part of the copper chloride-alkali metal chloride catalyst mixture.

In U.S. Pat. No. 4,463,200 it has been disclosed that in the manufacture of perchloroethylene by oxychlorination the use of an activated alumina having a surface area of at least 100 m$^2$/g and preferably between 150 and 250 m$^2$/g as the support for the copper chloride-potassium chloride catalyst mixture results in a significant reduction in the formation of undesirable by-products such as 1,1,2-trichloroethane or 1,1,1,2-tetrachloroethane and that this kind of high-surface-area support simultaneously also favors a high molar ratio of perchloroethylene to trichloroethylene in the product with excellent chlorine utilization. Unfortunately, such catalyst compositions using a high-surface-area support have also been found to promote excessive burning of the feedstock, that is, they destroy a substantial portion of the feedstock by converting it to oxides of carbon.

It has now been surprisingly discovered that an improved copper chloride-alkali metal chloride catalyst composition for the manufacture of trichloroethylene and perchloroethylene by oxychlorination in a fluidized bed can be obtained by using as a catalyst support an activated alumina possessing a closely controlled surface area which is in excess of 20 m$^2$/g but below 100 m$^2$/g, preferably between about 20 m$^2$/g and about 80 m$^2$/g, and most preferably between about 25 and 60 m$^2$/g. When such a support is loaded with a proper amount of a catalytic mixture of copper chloride and alkali metal chloride, e.g., a chloride of sodium, potassium or lithium (most preferably potassium chloride) and used as a catalyst in a fluidized state in the manufacture of trichloroethylene and perchloroethylene by oxychlorination, overall feed conversions are significantly improved along with a substantial and unexpected reduction in metal reactor corrosion rates. Low reactor corrosion rates are of course greatly desired but have been heretofore difficult to achieve in combination with high performance.

In one of its further aspects the invention relates to the preparation and use of oxychlorination catalysts possessing improved resistance to degradation of the catalyst structure during its use in a high temperature oxychlorination process. Most commercial fluid bed oxychlorination processes for the production of ethylene dichloride from ethylene are best conducted at temperatures below 300° C., i.e., at relatively low temperatures, and employ catalysts based on substantially pure high-surface area alumina supports. Other such processes use naturally occurring minerals, such as Fuller's earth or other clays, for catalyst supports. To be commercially useful, catalysts used in oxychlorination processes must have long-term surface area stability, as otherwise they become inoperable because of stickiness from salt overload when the surface area of the catalyst support becomes excessively reduced. Loss of surface area in alumina catalyst supports usually occurs because of a phase change from the gamma phase to the more dense alpha-alumina phase, which typically has very low surface areas.

In making perchloroethylene and trichloroethylene by oxychlorination of $C_2$ hydrocarbon, substantially higher reaction temperatures, of around 370° to 470° C., are required than in the manufacture of ethylene dichloride. Temperatures in the vicinity of 1200° C. are generally considered necessary to produce alpha-alumina from the gamma phase[1]. However, it has been reported that the gamma to alpha transition can be achieved in the 375°-425° C. range by hydrothermal treatment, but only under high pressures of several hundred pounds per square inch (more than 13 atmospheres)[2]. HCl has also been reported to cause the transition from gamma to alpha-alumina at well below 1200° C., e.g., at 850° C.[3] The logical expectation has been that the stability of an alumina-based catalyst at low pressures, e.g. less than 100 psig (about 7 atmospheres), would be substantially as good in an oxychlorination process conducted at around 370° or 470° C. as it has been known to be in oxychlorination processes conducted at or below 300° C.

[1] Karl Wefers et al, "Oxides and Hydroxides of Alumina," Tech. Paper No. 19, Alcoa Research Laboratories, 1972, Table 14, page 43.
[2] Allen S. Russell, "Alumina Properties," Tech. Paper No. 10, Alcoa Research Laboratories, 1953, page 6.
[3] Gitzen, "Alumina as a Ceramic Material," American Ceramic Society, Columbus, Oh., page 24

However, this expectation has been found to be misplaced. The simultaneous presence of steam and HCl in an oxychlorination process apparently can effect the transition from gamma to alpha-alumina at even lower temperatures, since we have observed a large decrease in surface area, from 73 m²/g to 9 m²/g, in a copper chloride-potassium chloride catalyst composition based on a gamma-alumina support in only 288 hours under oxychlorination conditions of 418° C. and 60 psig (about 4 atmospheres) pressure. Such a thermochemical degradation of conventional oxychlorination catalyst compositions at temperatures approaching or above 400° C. can make the oxychlorination reaction uneconomical in producing perchloroethylene and trichloroethylene.

It has now been found that oxychlorination catalysts based on gamma-alumina supports can be significantly improved in terms of their resistance to thermochemical degradation at or above 400° C. when a minor proportion, ranging from 0.2 to 10 percent and preferably 0.5 to 2.0 percent, of silica is incorporated in the alumina. Such concentrations of silica have been found to produce no significant effect on the properties of the support in a manner which is adverse to the desired functioning of the oxychlorination process when producing perchloroethylene and trichloroethylene. Good stability has been observed with supports which have been prepared with the addition of the silica either before the original spray-drying of the alumina gel from which the microspheroidal catalyst support particles are conventionally prepared or by impregnation with silica after such spray-drying (see, for example, U.S. Pat. No. 4,342,988), followed by calcination of the dry, impregnated alumina. However, other known ways may be used for including the desired small amount of silica into the alumina, i.e., for providing a silicated alumina as part of this oxychlorination catalyst.

In accordance with the present invention, the catalytic metal salts are loaded onto the supports possessing the selected surface area at a concentration of 10 to 25 percent, with the weight ratio of copper (II) chloride to potassium chloride in the catalytic salt mixture being from 0.5:1 to 3.0:1. The most suitable amount of the catalytic salts used for any particular catalyst is dependent on the surface area of the support. While supports having a surface area greater than 100 m²/g can support up to 30 or 35 weight percent copper chloride and potassium chloride salts without experiencing fluidization problems, it has been found that such relatively high catalyst loadings cause the microspheroidal catalyst particles to become sticky and difficult to maintain in the fluidized condition if loaded onto a support that has a surface area which is substantially lower than 100 m²/g from the beginning or which is reduced to below this value during use at elevated temperature. Accordingly, for a catalyst support having a surface area in the range called for by the present invention, i.e., in excess of about 20 and less than 100 m²/g, a total salt loading of between about 10 and 25 percent based on the weight of the finished catalyst should be used, or in the most preferable surface area range, i.e. between about 25 and 60 m²/g, a total salt loading between 15 and 19 percent based on the weight of the finished catalyst should be used. These ranges are consistent with the graph represented in FIG. 2.

In calculating the weight ratio of copper chloride to potassium chloride, the copper chloride is calculated as cupric chloride ($CuCl_2$). Thus, the term "calculated as $CuCl_2$", as used in the specification and claims herein, means that where cupric chloride ($CuCl_2$) is employed in the catalyst mixture, e.g., to obtain a copper chloride to alkali metal chloride ratio of 1.2:1, 1.2 g of cupric chloride are employed per gram of potassium chloride; and where cuprous chloride (CuCl) is employed in the catalyst mixture instead of $CuCl_2$, in order to obtain the same nominal copper chloride to potassium chloride ratio of 1.2:1, enough cuprous chloride must be employed such that, upon conversion of the cuprous chloride to cupric chloride in the oxychlorination reaction, 1.2 grams of reacted cupric chloride will be present in the catalyst composition per gram of potassium chloride.

The oxychlorination reaction is carried out using (1) a $C_2$ hydrocarbon (as earlier defined) as the organic feedstock, (2) chlorine and/or a chlorine-containing gas such as hydrogen chloride as a source of chlorine, and (3) an oxygen-containing gas such as molecular oxygen or air or oxygen-enriched air as a source of oxygen, with such gases entering the reaction zone at a combined velocity above the minimum fluidization velocity of the catalyst. The ratio of $C_2$ feed and chlorine-containing feed can be varied to control the degree of chlorination as suggested earlier hereinabove, thus achieving the desired trichloroethylene/perchloroethylene product split. The reaction is carried out within a temperature range of 370° to 470° C., preferably 400° to 430° C., with a contact time of 2 to 60 seconds, preferably 5 to 30 seconds. The reaction pressure may range from 1 to 20 atmospheres (absolute).

USE OF ALUMINA SUPPORT POSSESSING AN INTERMEDIATE SURFACE AREA

EXAMPLE 1

Catalyst Preparation

A microspheroidal alumina support having a surface area of 27 $m^2/g$ was prepared by calcination for 1 hour at a high temperature, i.e., 1050° C., of a commercially available microspheroidal gamma-alumina which had a surface area of 186 $m^2/g$, an average particle size of 63 microns, a silica content of less than 0.1 percent, a sodium oxide content of 0.04 percent and an iron oxide content of 0.04 percent.

To prepare the desired catalyst composition, an 816.8 gram portion of the calcined alumina support was placed in a heavy-gauge plastic bag. An aqueous solution containing 98.1 grams of copper (II) chloride dihydrate, 31.0 grams of potassium chloride and 400 grams of water was then added to the alumina in the bag. Sufficient solution was present to moisten all of the alumina. The preparation was thoroughly mixed by hand kneading, placed in a glass dish and dried overnight at 150° C. The dried catalyst composition contained 8.54 percent copper chloride and 3.88 percent potassium chloride. Target loadings for this catalyst were 8.35 and 3.35 percent copper chloride and potassium chloride, respectively, as calculated by the total weight of the anhydrous metal chlorides and the alumina support.

Other supports with surface areas of 5 and 85 $m^2/g$, respectively, were prepared from the same commercial high-surface-area alumina by calcination at 1200° C. for 1 hour (for Catalyst B) and at 1000° C. for 1.17 hours (for Catalyst C), respectively. Table I presents data on salt loadings of catalysts prepared similarly as described above from the parent alumina (Catalyst D) and the various calcined supports of various surface areas (Catalysts A, B and C).

TABLE I

| Catalyst | Support Surface Area ($m^2/g$) | Salt Loading, Wt % CuCl₂ | Salt Loading, Wt % KCl |
|---|---|---|---|
| A | 27 (Invention)* | 8.35 | 3.35 |
| B | 5 (Too Low)* | 7.50 | 2.50 |
| C | 85 (Borderline)* | 10.58 | 5.58 |
| D | 186 (Too High)** | 15.00 | 10.00 |

*Calcined
*Not Calcined.

EXAMPLE 2

Fluidized Bed Oxychlorination to Perchloroethylene and Trichloroethylene, 3.4 cm Reactor The fluidized bed reactor employed in this work was of Pyrex glass construction having a reaction zone 1.34 inches (3.4 cm) in diameter and 4 feet (122 cm) in length and a secondary expansion zone 2.5 inches (6.4 cm) in diameter and 8 inches (20.3 cm) in length. The reactor was fitted with an 8 mm glass thermocouple well extending through the top of the reactor to within 0.5 inches (1.3 cm) of the glass feed distributor frit at the bottom of the reaction tube. Metal corrosion rates were measured by recording the weight loss of metal coupons after exposure to the fluidized oxychlorination catalyst at reaction conditions for 50 hours. Since nickel and Inconel alloys are the materials of choice for construction of oxychlorination reactors operating at temperatures in the range from 370° to 470° C., Inconel 600 and Nickel 200 coupons, sized 0.5 inches×2 inches ×0.15 inches (1.3 cm×5.1 cm×0.4 cm), were suspended from the glass thermocouple well by Chromel A wire hooks. The coupons were located one foot (30.5 cm) above the feed distributor frit. The tubular reactor was placed inside a second glass tube with an inside diameter of 1.65 inches (4.2 cm) and a length of 4 feet (121.9 cm) wrapped with Chromel A heating wire. The temperature of the catalyst bed was controlled by varying the voltage applied to the heating wire. Ethylene, hydrogen chloride and air feed were preheated to 150° C. and mixed in a tee 6 inches (15.2 cm) below the glass distributor frit.

In a typical run, sufficient catalyst (about 750 ml) was charged to the reactor to provide a bed height of about 3.5 feet (106.7 cm). A superficial linear feed gas velocity of 0.28 feet per second (8.5 cm/sec) was employed. All tests were conducted at atmospheric pressure.

Results of oxychlorination runs obtained with the catalyst of the invention and other catalysts are listed in Table II.

TABLE II

Oxychlorination of Ethylene to Trichloroethylene and Perchloroethylene

| Run No. | 1 | 2 | 3 | 4 |
|---|---|---|---|---|
| Catalyst | A | B | C | D |
| Support Surface Area (square meters per gram) | 27 | 5 | 85 | 186 |
| Reaction Temperature, °C. | 420 | 419 | 420 | 419 |
| Feed Ratios, HCl/O₂ | 1.57 | 1.59 | 1.59 | 1.59 |
| Feed Ratio, HCl/C₂H₄ | 2.89 | 2.89 | 2.89 | 2.89 |
| Superficial Linear Velocity, cm/sec | 8.5 | 8.5 | 8.5 | 8.5 |
| HCl Conversion, percent | 94.05 | 95.11 | 83.75 | 64.7 |
| Ethylene Selectivity to: | | | | |
| Trichloroethylene | 47.48 | 62.86 | 42.61 | 25.62 |
| Perchloroethylene | 12.55 | 8.24 | 21.34 | 11.77 |
| Carbon oxides | 15.73 | 9.49 | 21.16 | 26.27 |
| Coupon Corrosion Rates: (mils per year) | | | | |
| Nickel 200 | 51.3 | 92.5 | 48.8 | 41.2 |
| Inconel 600 | 67.6 | 166 | 71.0 | 43.4 |

Figure 3:
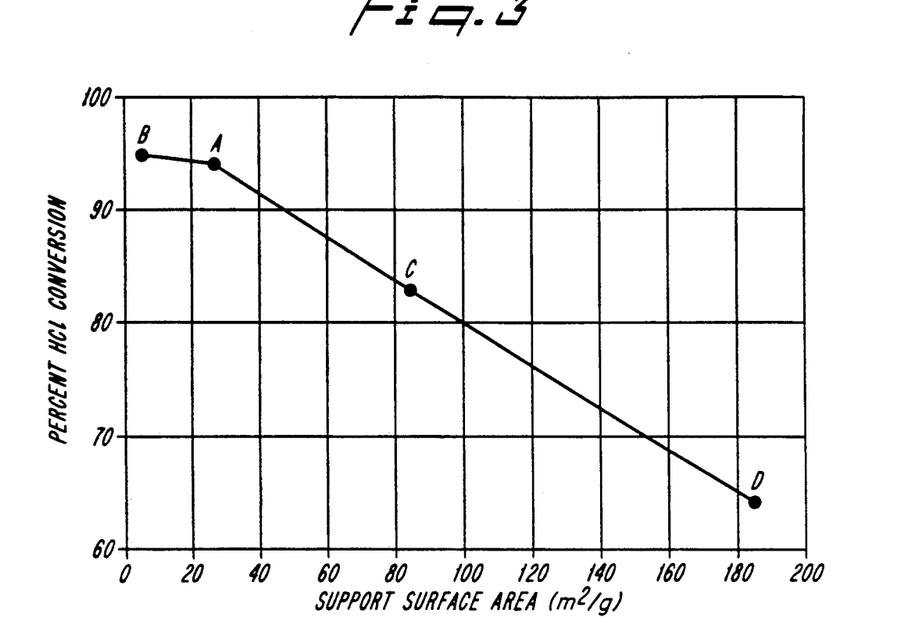
FIG. 3 is a graph showing the correlation between HCl conversion and the surface area of the catalyst support.
Figure 4:
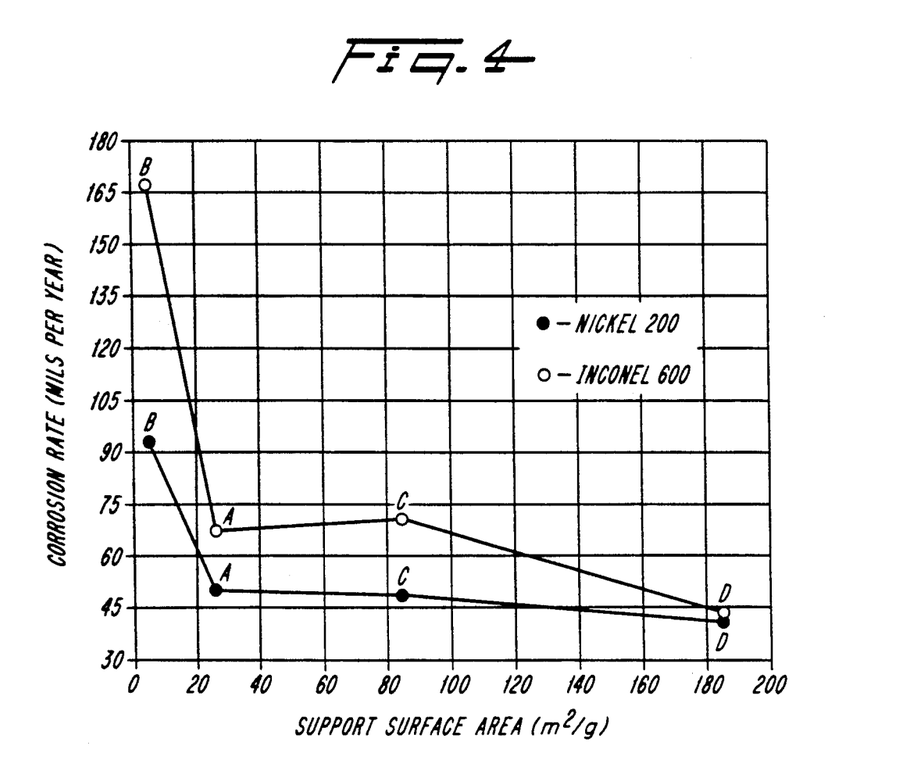
FIG. 4 is a graph showing the correlation between metal corrosion rates and the surface area of the catalyst support.

The results of the runs reported in Table II are illustrated in FIGS. 3 and 4. FIG. 3 is a plot of HCl conversion versus support surface area, and FIG. 4 is a plot of metal coupon corrosion versus catalyst support surface area.

HCl conversion is defined as:

100×(wt HCl in feed−wt HCl in reactor effluent)/wt HCl in feed.

A relatively low HCl feed rate was deliberately selected for these runs in order to favor making more trichloroethylene (TCE) than perchloroethylene (PCE). However, the process is flexible in this respect, and a higher ratio of HCl in the feed may be used if one wishes to make more PCE. The present invention is of particular value under reaction conditions favoring the production of TCE, as these conditions usually result in high burning of the hydrocarbon feed, and the novel catalyst compositions of this invention tend to reduce such burning.

FIG. 3 shows that HCl conversions increase dramatically as the surface area of the alumina catalyst support is decreased. "A", the preferred catalyst (support surface area 27 m²/g), exhibits a very high HCl conversion of 94.05 percent, better than that recorded with catalyst "C" (support surface area, 85 m²/g), and dramatically better than that recorded with catalyst "D", (support surface area, 186 m²/g). Catalyst "B" (support surface area, 5 m²/g) gave a slightly better HCl conversion (95.11 percent) than the preferred catalyst "A", but resulted in a vastly greater metal corrosion rate. Along with the improvement in catalyst performance as reflected in a better HCl conversion, the use of catalyst "A" has resulted in an unexpected reduction in corrosion rate in comparison with catalyst "B".

In FIG. 4 the corrosion rates for Nickel 200 and Inconel 600 coupons are plotted versus the surface areas of the catalyst supports. Corrosion rates in mils are based on a 360-day year as follows:

$$\text{Rate, mils per year} = \frac{\text{Delta} \times f \times T^i \times (360 \times 24)}{Wt^1 \times H}$$

where Delta=change in weight in grams, f=Coupon face area=total coupon surface area divided by 2, $T^i$=initial coupon thickness in mils, $Wt^i$=initial coupon weight in grams, and H is the total run time.

FIG. 1 showed that catalyst "B", having the lowest support surface area, gave the highest HCl conversion of 95.11 percent versus 94.05 for catalyst "A" of the invention. However, FIG. 4 shows that the corrosion rate was much greater in the case of catalyst "B" for both nickel and Inconel metal coupons. In summary, catalyst "A" resulted in a significantly higher HCl conversion than either catalyst "C" or especially catalyst "D", and at the same time catalysts "A" and "C" resulted in a corrosion rate far below that obtained with catalyst "B".

Perchloroethylene and trichloroethylene may be recovered from the reaction product stream by any suitable technique known to those skilled in the art. Thus, the effluent from the reactor may be passed through a cooler and a condenser to a phase separator which collects the condensed chlorohydrocarbons and hydrochloric acid. The chlorohydrocarbon stream from the phase separator may then be neutralized, dried, and sent to a fractional distillation system for purification and recovery of perchloroethylene and trichloroethylene.

EXAMPLE 3

Effect of Silica Addition

Catalyst Preparation and Aging, 5.1 cm Reactor 3050 gram samples of various commercially prepared microspheroidal alumina supports I, II and III, each of which possessed a specified content of silica, were placed in heavy-gauge plastic bags. An aqueous solution of 773.2 grams of copper (II) chloride dihydrate, 406.6 grams of potassium chloride and 1455 grams of water was then added to the alumina in each of the bags. Sufficient solution was present in each case to moisten all of the alumina. The preparations were thoroughly mixed by hand kneading, placed in glass dishes and dried overnight at 150° C. Target loadings for these catalysts were 15.0 and 10.0 weight percent copper chloride and potassium chloride, respectively, as calculated by the total weight of the anhydrous metal chlorides and the alumina support.

The alumina supports tested had the surface area characteristics and silica concentrations shown in Table III below. The initial surface area of each such complete catalyst composition, as well as the final surface area of each after a stated number of hours on stream in an oxychlorination run, are also shown in Table III.

Catalyst charges and specified feeds were introduced in the quantities and at the rates shown in Table IV below, which also shows the reaction conditions used in each run.

TABLE III

Properties of Supports and Catalysts Before and After Reaction Aging

| Support | % Silica | Initial Surface Area (m²/g) Support | Initial Surface Area (m²/g) Catalyst | Final Surface Area (m²/g) Run Time (hours) | Final Surface Area (m²/g) Catalyst |
|---|---|---|---|---|---|
| Alumina I* | <0.1 | 186 | 73 | 299$^a$ | 9.0 |
| Alumina II | 0.2 | 166 | 72 | 540$^a$ | 16.0 |
| Alumina III | 1.6 | 189 | 84 | 385$^b$ | 75.2 |

*Alumina I is the same material which was used, as such, as the support in catalyst D, Table I, and which was calcined to make the supports used in the catalysts A, B and C in Table I.
$^a$Catalyst life test run in the 15.2 cm diameter reactor.
$^b$Catalyst life test run in the 5.1 cm diameter reactor.

TABLE IV

Average Run Conditions for Oxychlorination Catalyst Life Studies

| Reaction Parameter | 5.1 cm Reactor | 15.2 cm Reactor |
|---|---|---|
| Catalyst Charge, kg | 4.1 | 38.6–61.3 |
| Temperature, °C. | 410 | 418 |
| Pressure, atm. | 4.1 | 4.1 |
| Catalyst Bed Height, cm | 259 | 274–396 |
| Superficial Linear Velocity, | 18.3 | 18.3 |
| Residence Time, seconds | 14 | 14–22 |
| HCl/Ethylene Dichloride Molar Ratio | 1.2–1.65 | 1.35 |
| HCl/Oxygen Molar Ratio | 0.96 | 0.95 |
| When Ethylene Was Fed: | | |
| HCl/Ethylene Molar Ratio | — | 2.85 |
| HCl/Oxygen Molar Ratio | — | 1.60 |

EXAMPLE 4

Catalyst Preparation and Aging, 15.2 cm Reactor

In another series of runs, 42 kg quantities of various commercially prepared microspheroidal alumina supports were placed in an epoxy-coated steel tray capable of being heated with steam pipes fastened beneath it. An aqueous solution of 10.7 kg of copper (II) chloride dihydrate, 5.6 kg of potassium chloride and 20.1 kg of water was poured over the alumina in the tray and mixed in thoroughly with a small rake. The catalysts were dried to a uniform brown color with 120 pound (8 atm.) steam in the heating pipes under the tray. Target loadings for these catalysts were the same as in Example 3. The alumina supports I and II had the surface area characteristics, initial and aged, and the silica concentrations indicated in Table III above.

EXAMPLE 5

Test of Catalyst Life in a 5.1 Centimeter Diameter Fluidized-Bed Oxychlorination Reactor The selected catalyst charge was loaded into a pressurizable reactor fabricated from 5.1 cm diameter pipe 396 cm in length made of Inconel 600 nickel-chromium alloy. Welded around the reactor tube was a pressurized 10.2 cm pipe jacket connected into a thermosyphon filled with Dowtherm A heat transfer medium (b.p. 258° C.) for cooling. The reactor was equipped with a distributor at the bottom and an enlargement at the top. The enlargement was 15.2 cm in diameter and 122 cm long, tapering downward to its flange connection with the 5.1 cm diameter reactor tube. The effluent line was equipped with a cyclone, fines pot, fines filter and pressure control valve. A 0.6 cm Inconel tube extending the length of the reactor tube contained a sliding thermocouple. The reactor, effluent line and accessory equipment were electrically heated and insulated.

In the course of each oxychlorination run the reactor was shut down and depressurized for periodic removal of catalyst samples for surface area analysis.

EXAMPLE 6

Test of Catalyst Life in a 15.2 cm Diameter Fluidized-Bed Oxychlorination Reactor The selected catalyst charge was loaded into a pressurizable reactor fabricated from 15.2 cm diameter Inconel 600 pipe 396 cm in length. Welded into the top and bottom of this reactor section were four 1¾ inch (1.9 cm diameter) tubes running the length of the section and standing out 2.5 cm from the wall. Dowtherm A heat transfer medium was circulated through these tubes for cooling. A distributor was flanged to the bottom of the reactor section and an enlargement section to the top. The enlargement tapered from the six inch (15.2 cm diameter) pipe section through a 60 degree cone into a cylinder 16 inches (40.6 cm) in diameter and 24 inches (61 cm) high. The effluent line of this reactor was equipped with a cyclone with a catalyst return leg, a fines filter and a pressure control valve. Thermocouple wells were welded into the side of the reactor tube at various levels. The reactor and accessory equipment were electrically heated and insulated.

Catalyst charges and specified feeds were introduced in the quantities and rates prescribed in Table IV above, which also shows the run conditions. Catalyst samples were removed periodically through a valve without shutdown for surface area analysis.

Figure 5:
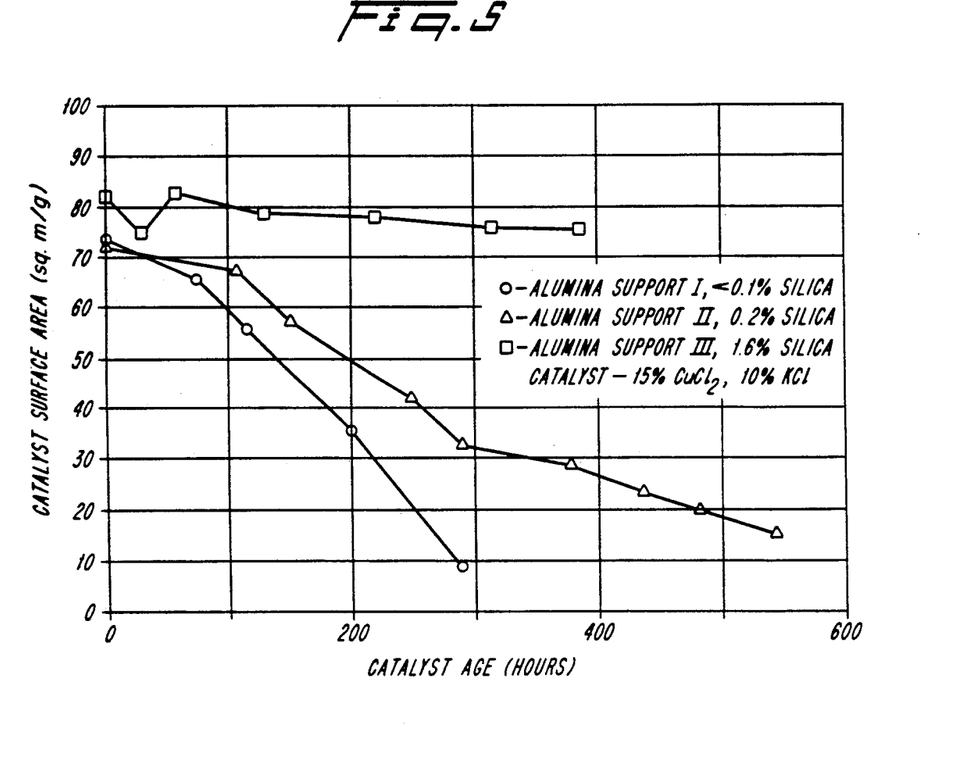
FIG. 5 is a graph showing the loss of surface area of three different catalysts after aging in the process.

The data shown in Table III are illustrated graphically in FIG. 5 where the surface areas of three catalysts are plotted against the aging time in actual oxychlorination runs. Clearly, increased amounts of silica considerably lessened the rate of surface area decrease with respect to time, showing that increased stability can be imparted by the inclusion of larger amounts of silica in the catalyst support. All of the aluminas in Table III contained silica which was either present in the original alumina gel or was added before the alumina was activated by heating to around 600° C.

Figure 6:
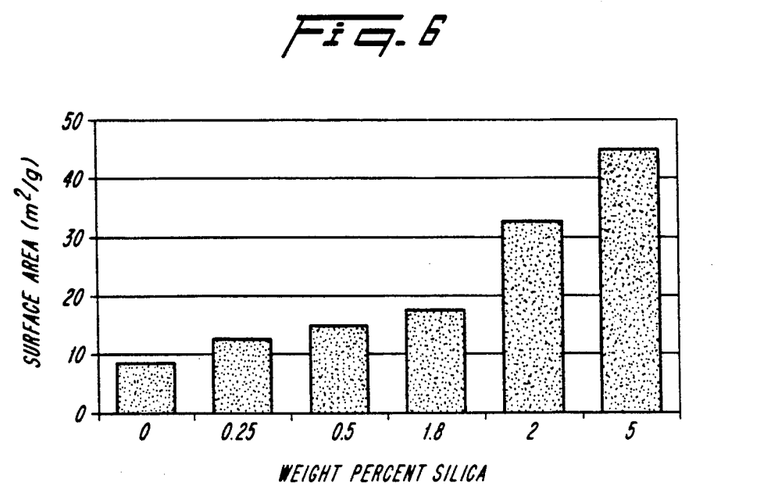
FIG. 6 is a bar chart showing the effect of silica content on the thermal stability of the support.

Various samples were prepared from Alumina I (Table III), which had an initial surface area of 186 $m^2/g$, by adding to it different amounts of silica in the form of silicone oil and then heating each in a furnace at 1200° C. for three hours. Stabilization of alumina by adding silicone oil to it is described in U.S. Pat. No. 4,392,988. The effects on surface area of the resulting supports are shown in Table V below and in FIG. 6.

Table V shows a direct correlation of support stabilization (as measured by surface area after calcination at 1200° C.) with the amount of silica added to Alumina I. The results in Table V also correlate very favorably with the data in Table III relating oxychlorination run time with the final surface area, and confirms that the purely thermal method of calcining at 1200° C. provides a valid method for accelerated testing of catalyst supports.

TABLE V

Effect of 1200° C. Calcination on Silicone-Oil Treated Alumina Supports

| Weight Percent Silica Added | Surface Area, $m^2/g$ |
|---|---|
| 0.0 | 8.0 |
| 0.25 | 12.8 |
| 0.5 | 15.1 |
| 1.8 | 17.4 |
| 2.0 | 32.8 |
| 5.0 | 45.0 |

In comparing Table V with Table III, one should keep in mind that the results in Table V were obtained when surface area stability was tested in an accelerated thermal test by calcining the various alumina supports by themselves at 1200° C., whereas the results in Table III were obtained when the various compositions identified there were used as catalysts in an oxychlorination reaction conducted at 410° to 418° C. A comparison between these two sets of results shows that the accelerated thermal test conducted at 1200° C. provides a good measure of the surface area stability that a particular catalyst support can be expected to exhibit under actual oxychlorination reaction conditions.

Similarly, while the catalysts tested in Examples 5 and 6 above were prepared using alumina supports that possessed an initial surface area in excess of 160 $m^2/g$, i.e., well above the upper limit of the present invention, these tests nevertheless clearly demonstrate the beneficial effect of controlled silica addition on the thermal or thermochemical stability of these alumina-base catalyst compositions at high temperatures under oxychlorination or calcination conditions, and serve as useful evidence that controlled silica addition will have this same beneficial effect in the case of alumina or alumina-silica supports falling within the scope of this invention, i.e., supports characterized by an initial surface area below 100 $m^2/g$, i.e., 20 to 100 $m^2/g$, or more particularly 25 to 60 $m^2/g$.

Use of Predetermined Amount of Magnesium Chloride

According to yet another and particularly preferred refinement of the invention an improved catalyst composition of the general type described above is provided which has a good catalyst life, keeps reactor corrosion low and is especially effective in producing a high proportion of either perchloroethylene or trichloroethylene with only small burning losses and with accompanying increases in the total efficiency of the reaction under the conditions best suited for producing either product.

The process of making perchloroethylene and trichloroethylene by catalytic oxychlorination of $C_2$ hydrocarbons and their partially chlorinated derivatives is an especially complex one. In addition to the requirement for a catalyst and reaction conditions favoring chlorination of the organic feed at a rapid rate, there is a necessity for the chlorinated intermediates produced to be dehydrochlorinated at a rapid rate to allow further chlorination. With all of this, different catalysts as well as different reaction conditions are usually required to optimize the production of perchloroethylene or trichloroethylene. Processes for oxychlorinating $C_2$ hydrocarbons and their derivatives have been commonly known to destroy a substantial proportion of the organic feed through its conversion to carbon oxides. Trichloroethylene production is especially sensitive to high burning rates and requires care in the choice of catalyst and conditions.

In searching for compounds that would stabilize alumina supports against loss of surface area in the high-temperature environment of the oxychlorination reaction used to make perchloroethylene and trichloroethylene, it has now been unexpectedly found that magnesium chloride, or other magnesium compounds such as magnesium acetate or magnesium nitrate, added in the proper proportion to a catalyst possessing the characteristics described earlier herein gives improved performance in the form of reduced burning and usually also produces other improvements in terms of increased hydrogen chloride or chlorine conversion and higher selectivity to perchloroethylene and trichloroethylene. The improvement in performance has been found to be especially marked with feed ratios appropriate for the production of trichloroethylene.

The catalyst according this embodiment of the invention is composed of copper (II) chloride, potassium chloride and magnesium chloride on supports consisting essentially of at least 90 and up to 99.8 weight percent alumina and at least 0.2 and up to 10 weight percent silica. As previously stated herein, the weight ratio of potassium chloride to magnesium chloride is in the range from 0.8:1 to 1.2:1 in its preferred embodiment and is most preferably close to 1, irrespective of the surface area of the support. The proper proportions of the several components of the catalyst salt mixture as well as proper loading of the salt mixture on the support is determined from equations (1) and (2) listed in an earlier portion of this specification.

The useful range of support surface areas described by the above equations is about 10 to 250 $m^2/g$ of support, but the present invention requires the use of supports having a surface area between 20 and 100 $m^2/g$, most preferably between 25 and 60 $m^2/g$, as described earlier.

The following examples illustrate the invention using ethylene dichloride as the organic feed in the production of perchloroethylene and trichloroethylene, but the improvement is just as valid when ethylene, ethane or any of their partially chlorinated derivatives are used as feeds.

EXAMPLE 7

Catalyst Preparation

An aqueous solution of 131.7 g of copper (II) chloride dihydrate, 93.5 g of magnesium chloride hexahydrate and 43.8 g of potassium chloride in 480 g of water was prepared and added to a heavy-gauge plastic bag containing 1008 g of a microspheroidal alumina support containing 97 weight percent alumina, 1.6 weight percent silica and the balance mostly volatile materials. The average particle size was 50–60 microns and its surface area was 35 $m^2/g$.

The constituents were kneaded to a uniform color and consistency in the closed bag. Sufficient solution was present to create the consistency of dough. The uniform mixture was placed in a glass dish in an oven at 150° C. and dried overnight. The target composition for this catalyst in weight percentages was copper (II) chloride, 8.65; potassium chloride, 3.65; magnesium chloride, 3.65; all calculated on the basis of the weights of anhydrous metal chloride and the alumina support.

Catalysts prepared on silicated alumina supports having surface areas of 56 and 228 $m^2/g$ were prepared by similar procedures. The higher surface area catalysts required somewhat higher proportions of water to maintain a slightly moist consistency. Table VI shows data on the surface areas of the alumina supports and their corresponding metal salt loadings.

TABLE VI

| Support | Surface Area $m^2/g$ | % Silica | Salt Loading, weight percent | | |
|---|---|---|---|---|---|
| | | | $CuCl_2$ | KCl | $MgCl_2$ |
| Alumina IV | 35 | 1.6 | 8.65 | 3.65 | 3.65 |
| Alumina V | 56 | 2.0 | 9.50 | 4.50 | 4.50 |
| Alumina VI | 228 | 5.0 | 10.00 | 12.48 | 12.48 |

All three supports in Table VI contained the stated concentration of silica incorporated into the support by the manufacturer before calcination. Alumina IV was calcined to 35 $m^2/g$ by the manufacturer. Alumina V was also calcined by its manufacturer, which was different from that of Alumina IV. Alumina VI was an uncalcined but activated high-surface-area alumina prepared by the manufacturer of Alumina IV.

EXAMPLE 8

Fluidized Bed Oxychlorination to

Perchloroethylene and Trichloroethylene

The fluidized bed reactor used was made of Pyrex glass, electrically heated and insulated, and had a reaction zone 3.4 cm in diameter and 122 cm long with an expansion zone 6.4 cm in diameter and 20.3 cm long. An 8 mm thermocouple well extended from the top of the reactor to 1.3 cm above the fritted disk distributor plate in the bottom. The catalyst bed was 116 to 122 cm in height. The superficial linear velocity was about 9.1 cm per second, and the residence time was about 13 seconds. Ethylene dichloride (EDC) vapor, HCl and air were fed through the frit. For a high-ratio run (HCl/EDC=1.68) 0.451 moles per hour of EDC were fed through the frit with the appropriate number of moles of HCl and air at an $HCl/O_2$ ratio of 0.95. For a low-ratio run (HCl/EDC=1.20), 0.605 moles per hour of EDC were fed with the proper number of moles of HCl and air at the same $HCl/O_2$ ratio of 0.95. The reactor was run at ambient pressure at a temperature of 410° C. The results are shown in Tables VII, VIII and IX.

TABLE VII

Comparison of Catalysts on Support IV, Surface Area - 35 m²/g Atmospheric Pressure Runs

| Run Number | 1 | 2[a] | 3[b] | 4[b] | 5[b] |
|---|---|---|---|---|---|
| Catalyst Composition | | | | | |
| $CuCl_2$, Wt. % | 8.65 | 8.65 | 8.65 | 8.53 | 8.17 |
| KCl, Wt. % | 3.65 | 3.65 | 7.30 | 3.53 | — |
| $MgCl_2$, Wt. % | 3.65 | 4.67 | — | — | 7.82 |
| Total Loading, Wt. % | 15.95 | 16.97 | 15.95 | 12.06 | 15.99 |
| $KCl/MgCl_2$, Weight Ratio | 1.00 | 0.78 | inf. | inf. | 0.0 |
| $(KCl + MgCl_2)/CuCl_2$, Wt. Rat. | 0.84 | 0.96 | 0.84 | 0.41 | 0.96 |
| Catalyst performance: | | | | | |
| (A) High Feed Ratio: HCl/EDC = 1.68, $HCl/O_2$ = 0.95 | | | | | |
| HCl Conversion, % | 87.4 | 87.4 | 80.4 | 87.7 | — |
| Burning, % | 7.5 | 9.3 | 8.4 | 11.1 | — |
| PCE + TCE Selectivity[c], % | 76.8 | 79.4 | 80.7 | 80.7 | — |
| Efficiency[d] | 156.7 | 157.5 | 152.7 | 157.3 | — |
| (B) Low Feed Ratio: HCl/EDC = 1.20, $HCl/O_2$ = 0.95 | | | | | |
| HCl Conversion, % | 93.1 | 91.2 | 90.0 | 79.0 | 72.9 |
| Burning, % | 7.4 | 7.5 | 8.0 | 10.4 | 9.8 |
| PCE + TCE Selectivity[c], % | 70.4 | 70.1 | 72.1 | 57.1 | 58.7 |
| Efficiency[d] | 156.1 | 153.8 | 154.1 | 125.7 | 121.8 |
| Total Efficiency[e] | 312.8 | 311.3 | 306.8 | 283.0 | — |

[a]Ratio Comparison Run,
[b]Catalyst Composition Comparison Run
[c]PCE = Perchloroethylene, TCE = Trichloroethylene
[d]Efficiency = HCl Conversion + (PCE + TCE) Selectivity - Burning
[e]Total Efficiency = Efficiency at low feed ratio + Efficiency at high feed ratio Table VII shows the importance of catalyst formulations according to this invention on a support well within the preferred surface-area range of the invention and also stabilized with silica within the preferred range of the invention. In Run 1, the catalyst composition employed was very close to the ideal composition with respect to total loading and salt ratio as shown on the preferred lines of FIGS. 1 and 2. Run 1 had a Total Efficiency of 312.8, the highest observed on the 35 m²/g support. Because of the change of weight ratio of $KCl/MgCl_2$ to 0.78, slightly outside of the more desirable range of 0.8-1.2, in Run 2 the Total Efficiency dropped to 311.3, though still high. Run 3, employing the best of the binary catalysts shown, comprising cupric chloride with no magnesium chloride and with an amount of potassium chloride equal to the sum of potassium chloride and magnesium chloride in Run 1 (other binary catalysts $CuCl_2/KCl$ or $CuCl_2/MgCl_2$, are shown in Runs 4 and 5) gave a lower Total Efficiency at 306.8. Run 4 shows the inferior results obtained when the magnesium chloride was completely omitted from the catalyst of Run 1. Run 5 shows the results obtained at low feed ratios when magnesium chloride alone was used on the catalyst in approximately the same concentration as the cupric chloride, with no potassium chloride.

TABLE VIII

Comparison of Catalysts on Support V, Surface Area = 56 m²/g Atmospheric Pressure Runs

| Run Number | 6 | 7[a] |
|---|---|---|
| Catalyst Composition | | |
| $CuCl_2$, Wt. % | 9.50 | 9.00 |
| KCl, Wt. % | 4.50 | 4.00 |
| $MgCl_2$, Wt. % | 4.50 | — |
| Total Loading, Wt. % | 18.50 | 13.00 |
| $KCl/MgCl_2$, Wt. Ratio | 1.00 | inf. |
| $(KCl + MgCl_2)/CuCl_2$, Wt. Ratio | 0.95 | 0.44 |
| Catalyst Performance: | | |
| (A) High Feed Ratio: HCl/EDC = 1.68, $HCl/O_2$ = 0.95 | | |
| HCl Conversion, % | 84.4 | 64.9 |
| Burning, % | 11.5 | 16.1 |
| PCE + TCE Selectivity[b], % | 79.3 | 74.1 |
| Efficiency[c] | 152.2 | 122.9 |
| (B) Low Feed Ratio: HCl/EDC = 1.20, $HCl/O_2$ = 0.95 | | |
| HCl Conversion, % | 77.8 | 30.3 |
| Burning, % | 9.7 | 14.4 |
| PCE + TCE Selectivity[b], % | 62.8 | 50.5 |
| Efficiency[c] | 130.9 | 66.4 |
| Total Efficiency[d] | 283.1 | 189.3 |

[a]Catalyst Composition Comparison Run
[b]PCE = Perchloroethylene, TCE = Trichloroethylene
[c]Efficiency = HCl Conversion + (PCE + TCE) Selectivity - Burning
[d]Total Efficiency = Efficiency at low feed ratio + Efficiency at high feed ratio

TABLE IX

Comparison of Catalysts on Support VI, Surface Area = 228 m²/g Atmospheric Pressure Runs

| Run Number | 8 | 9[a] | 10[b] | 11[a] | 12[a] | 13[a] | 14[a] |
|---|---|---|---|---|---|---|---|
| Catalyst Composition | | | | | | | |
| $CuCl_2$, Wt. % | 10.04 | 15.00 | 15.00 | 13.06 | 7.86 | 9.74 | 10.32 |
| KCl, Wt. % | 12.48 | 10.00 | 10.00 | 10.97 | 13.57 | 8.42 | 16.45 |
| $MgCl_2$, Wt. % | 12.48 | 10.00 | — | 10.97 | 13.57 | 16.84 | 8.23 |
| Total Loading, Wt. % | 35.00 | 35.00 | 25.00 | 35.00 | 35.00 | 35.00 | 35.00 |
| $KCl/MgCl_2$, Weight Ratio | 1.00 | 1.00 | inf. | 1.00 | 1.00 | 0.50 | 2.00 |
| $(KCl + MgCl_2)/CuCl_2$, Weight Ratio | 2.49 | 1.33 | 0.67 | 1.68 | 3.45 | 2.59 | 2.39 |
| Catalyst Performance: | | | | | | | |
| (A) High Feed Ratio: HCl/EDC = 1.68, $HCl/O_2$ = 0.95 | | | | | | | |
| HCl Conversion, % | 87.3 | 84.4 | 84.8 | 82.3 | 63.9 | 87.1 | — |
| Burning, % | 8.7 | 10.9 | 16.3 | 13.4 | 8.8 | 15.3 | — |
| PCE + TCE Select.[c], % | 86.7 | 81.4 | 78.1 | 82.5 | 75.6 | 80.8 | — |

TABLE IX-continued

Comparison of Catalysts on Support VI, Surface Area = 228 m²/g
Atmospheric Pressure Runs

| Run Number | | 8 | 9[a] | 10[b] | 11[a] | 12[a] | 13[a] | 14[a] |
|---|---|---|---|---|---|---|---|---|
| | Efficiency[d] | 165.3 | 154.9 | 146.6 | 151.4 | 130.7 | 152.6 | — |
| (B) | Low Feed Ratio: HCl/EDC = 1.20, HCl/O₂ = 0.95 | | | | | | | |
| | HCl Conversion, % | 85.0 | 69.6 | 9.7 | 71.8 | 73.7 | 83.4 | 76.5 |
| | Burning, % | 9.0 | 13.4 | 22.2 | 12.7 | 8.2 | 10.9 | 10.7 |
| | PCE + TCE Select.[c], % | 79.6 | 63.7 | 40.4 | 69.3 | 76.4 | 72.6 | 72.0 |
| | Efficiency[d] | 155.6 | 119.9 | 27.9 | 128.4 | 141.9 | 145.1 | 137.8 |
| Total Efficiency[e] | | 320.9 | 274.8 | 174.5 | 279.8 | 272.6 | 297.7 | — |

[a]Ratio comparison run
[b]Catalyst composition comparison run
[c]PCE = Perchloroethylene, TCE = Trichloroethylene
[d]Efficiency = HCl Conversion + (PCE + TCE) Selectivity - Burning
[e]Total Efficiency = Efficiency at low feed ratio + Efficiency at high feed ratio Table VIII shows an example of the great improvement made by the addition of magnesium chloride to a binary catalyst composition on a support prepared by a different manufacturer, by a method which produced less than optimal chemical properties. A comparison is made between two catalysts prepared from this 56 m²/g surface-area alumina, which catalysts were found to be comparatively inferior in activity to those prepared from the support in Table VII. The catalyst of Run 6 had an ideal loading and salt ratios as described by the curves depicted in FIGS. 1 and 2 and is compared with a binary catalyst modeled after the binary catalyst of Run 4, Table VII and adjusted for support surface area (Run 7). Clearly an amount of MgCl₂ added in accordance with the preferred range of this invention caused an important increase in the Total Efficiency of the catalyst to an even greater degree than observed with closely analogous compositions in Table VII (Runs 4 and 1).

Table IX shows the value of appropriate combinations of CuCl₂ and KCl, with and without MgCl₂, as shown in Equation 1 and illustrated in FIGS. 1 and 2 with respect to the Total Efficiency described in Note (e) of the table in connection with oxychlorination runs conducted at atmospheric pressure. Run 8, with near-optimum (KCl+MgCl₂)/CuCl₂ and KCl/MgCl₂ ratios, gave the highest Total Efficiency and the least burning obtained at atmospheric pressure. However, in contrast to the preferred intermediate-surface area (35 m²/g) support of the invention described in Table VII, none of the catalysts based on the high-surface-area support of Table IX performed well at higher pressures, e.g. 4 atmospheres. Therefore, the results of the runs in Table IX must be regarded as relative values which are only directionally significant for operating under pressure. By comparison with Run 8 in Table IX Run 9 shows the adverse consequences of a low (KCl+MgCl₂)/CuCl₂ ratio in terms of lower Efficiency and higher carbon burning and Run 10 shows the even more unpropitious consequences of leaving out the magnesium chloride with otherwise the same catalyst as in Run 9. Runs 11 and 12 show the results of other high and low ratios of (KCl+MgCl₂)/CuCl₂ with the ratio KCl/MgCl₂ and the loading remaining at ideal values. Runs 13 and 14 show the effects on Total Efficiency of maintaining the ratio (KCl+MgCl₂)/CuCl₂ and the loading at the ideal values and using low and high ratios of KCl/MgCl₂.

It should be understood that while the foregoing description of the invention includes preferred embodiments and specific working examples, many variations and modifications of what has been described may be employed by those skilled in the art without departing from the scope or spirit of this invention. Such variations and modifications are to be considered within the scope of the appended claims.

What is claimed is:

1. In a process for the production of trichloroethylene and perchloroethylene by catalytic oxychlorination of a $C_2$ hydrocarbon or a partially chlorinated derivative thereof in a reaction zone comprising a fluidized bed of microspheroidal particles of catalyst maintained at a temperature between 370° and 470° C. and a pressure between 1 and 20 atmospheres and providing a superficial reaction zone residence time of 2 to 60 seconds, the improvement which comprises using as the catalyst a catalyst composition comprising a mixture of copper chloride, potassium chloride and magnesium chloride deposited in a catalytically active amount on a microspheroidal support comprising from 90 to 99.8 percent alumina and from 0.2 to 10 percent silica and having an initial surface area X in excess of 20 and less than 100 m²/g, (a) the ratio of copper chloride, to potassium chloride in said salt mixture being between 0.5:1 and 5.0:1, the copper chloride being calculated as copper (II) chloride and (b) the ratio of $MgCl_2$ to KCl in said salt mixture being between 0.5:1 and 2.0:1, said salt mixture being deposited on said microspheroidal support at a catalyst loading Y which is dependent on the initial surface area X of said microspheroidal support, wherein Y is calculated from the equation Y (expressed in weight
percent)=(0.102X+12.57)±20%, X being a figure corresponding to the initial surface area of the support expressed in square meters per gram.

2. A process according to claim 1, wherein the magnesium chloride is present in the salt mixture of the catalyst composition in a ratio between 0.95:1 and 1.05:1 relative to the potassium chloride.

3. In a process for making trichloroethylene by catalytic oxychlorination wherein a $C_2$ hydrocarbon or a partially chlorinated derivative thereof is reacted with an oxygen-containing gas and hydrogen chloride or chlorine in a reaction zone comprising a fluidized bed of microspheroidal particles of catalyst maintained at a temperature between about 400° and 430° C. and a pressure between 1 and 20 atmospheres and providing a superficial reaction zone residence time of 5 to 30 seconds, the improvement which comprises using as the catalyst a catalyst composition consisting essentially of a mixture of copper chloride, potassium chloride and magnesium chloride deposited on a microspheroidal support comprising from 98 to 99.5 percent alumina and from 0.5 to 2.0 percent silica and having an initial surface area between 25 and 60 m$^2$/g and an average particle size between about 30 and 70 microns, (a) the ratio of copper chloride to potassium chloride in said salt mixture being between 1.2:1 and 3.0:1, the copper chloride being calculated as copper (II) chloride, and (b) the ratio of MgCl$_2$ to KCl in said salt mixture being between 0.8:1 and 1.2:1, said salt mixture being deposited on said microspheroidal support at a catalyst loading Y which is in the range between about 10 about 25 percent and is dependent on the initial surface area X of said microspheroidal support, Y being calculated from the equation Y (expressed in weight percent) = (0.102X ± 20%

X being a figure corresponding to the initial surface area of the support expressed in square meters per gram.

4. A process according to claim 3, wherein the salt mixture contains copper chloride, potassium chloride and magnesium chloride in such proportions that the weight ratio of (potassium chloride + magnesium chloride) to copper (II) chloride in said mixture is not more than 0.00973X + 0.860 and not less than 0.00811X + 0.216, X being a figure corresponding to the initial surface area of the microspheroidal support expressed in square meters per gram.

5. A process according to claim 1, wherein said microspheroidal support particles consist essentially of between 95 percent and 99.5 percent alumina and correspondingly between 5 percent and 0.5 percent silica.

* * * * *